(12) United States Patent
Geitz et al.

(10) Patent No.: US 9,179,825 B2
(45) Date of Patent: Nov. 10, 2015

(54) POSITIONING SYSTEM FOR MANIPULATING A CHANNEL WITHIN A MEDICAL DEVICE

(71) Applicant: Boston Scientific Scimed, Inc., Maple Grove, MN (US)

(72) Inventors: Kurt Geitz, Sudbury, MA (US); Brian Tinkham, Scituate, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/312,208

(22) Filed: Jun. 23, 2014

(65) Prior Publication Data

US 2014/0303553 A1    Oct. 9, 2014

Related U.S. Application Data

(63) Continuation of application No. 12/882,719, filed on Sep. 15, 2010, now Pat. No. 8,795,156, which is a continuation of application No. 11/359,897, filed on Feb. 21, 2006, now Pat. No. 7,815,564.

(51) Int. Cl.
*A61B 1/00* (2006.01)
*A61B 1/005* (2006.01)
*A61B 1/018* (2006.01)

(52) U.S. Cl.
CPC ........... *A61B 1/0057* (2013.01); *A61B 1/00098* (2013.01); *A61B 1/00133* (2013.01); *A61B 1/018* (2013.01); *A61B 1/0052* (2013.01); *A61B 1/00066* (2013.01)

(58) Field of Classification Search
CPC ... A61B 1/0125; A61B 1/00098; A61B 1/018

USPC ......... 600/104, 106, 107, 123, 137, 139, 141, 600/142; 604/95.04
See application file for complete search history.

(56) References Cited

U.S. PATENT DOCUMENTS

| 4,245,624 A | 1/1981 | Komiya |
| 4,452,236 A | 6/1984 | Utsugi |
| 4,979,496 A | 12/1990 | Komi |

(Continued)

FOREIGN PATENT DOCUMENTS

| EP | 0 682 910 A | 11/1995 |
| EP | 1 302 151 A2 | 4/2003 |

(Continued)

OTHER PUBLICATIONS

International Search Report from PCT/US2006/045979 mailed Oct. 2, 2007 (5 pages).

*Primary Examiner* — Anhtuan T Nguyen
*Assistant Examiner* — Rynae Boler
(74) *Attorney, Agent, or Firm* — Bookoff McAndrews, PLLC

(57) ABSTRACT

Embodiments of the invention include a medical device for accessing a patient's body portion and used for diagnosis and treatment of medical conditions. Embodiments of the invention may include a particular endoscopic positioning mechanism for placing an endoscope and an additional treatment device within desired body portions in order to assist in diagnosis and treatment of anatomical diseases and disorders. In particular, a medical device according to an embodiment of the invention includes a positioning mechanism configured for movement through at least two degrees of freedom.

18 Claims, 10 Drawing Sheets

(56) References Cited

U.S. PATENT DOCUMENTS

| | | |
|---|---|---|
| 5,261,391 A | 11/1993 | Inoue |
| 5,351,678 A | 10/1994 | Clayton et al. |
| 5,460,168 A | 10/1995 | Masubuchi et al. |
| 5,520,678 A | 5/1996 | Heckele et al. |
| 5,957,937 A | 9/1999 | Yoon |
| 6,099,464 A | 8/2000 | Shimizu et al. |
| 6,152,870 A | 11/2000 | Diener |
| 6,277,064 B1 | 8/2001 | Yoon |
| 6,582,357 B2 | 6/2003 | Ouchi et al. |
| 6,605,033 B1 | 8/2003 | Matsuno |
| 6,824,509 B2 | 11/2004 | Yamaya et al. |
| 6,827,683 B2 | 12/2004 | Otawara |
| 7,063,659 B2 | 6/2006 | Goto et al. |
| 7,341,555 B2 | 3/2008 | Ootawara et al. |
| 2002/0091303 A1* | 7/2002 | Ootawara et al. ............. 600/106 |
| 2005/0096501 A1 | 5/2005 | Stelzer et al. |
| 2005/0131278 A1 | 6/2005 | Dickopp |

FOREIGN PATENT DOCUMENTS

| | | |
|---|---|---|
| EP | 1 586 275 A | 10/2005 |
| JP | 49-082188 A | 8/1974 |
| JP | 06-319680 | 11/1994 |

* cited by examiner

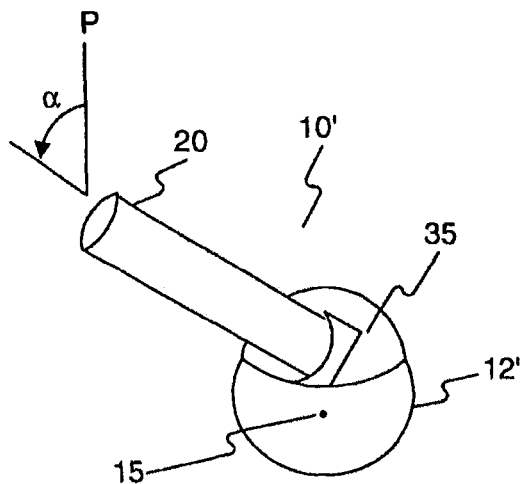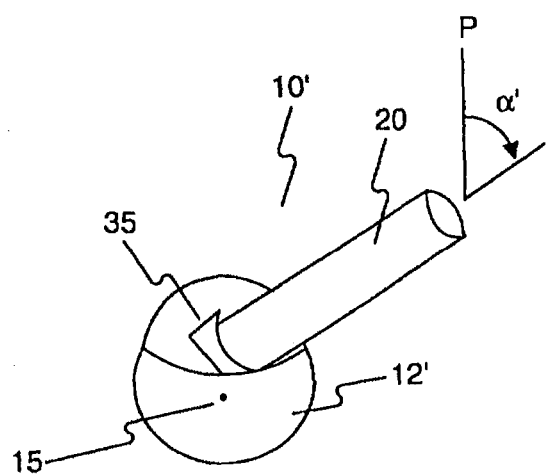
FIG. 5A  FIG. 5B
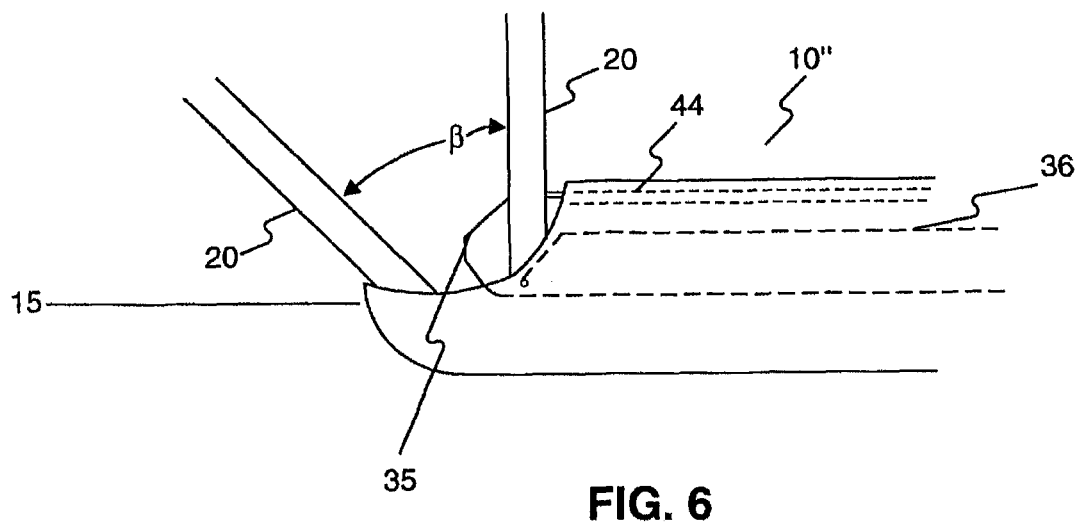
FIG. 6

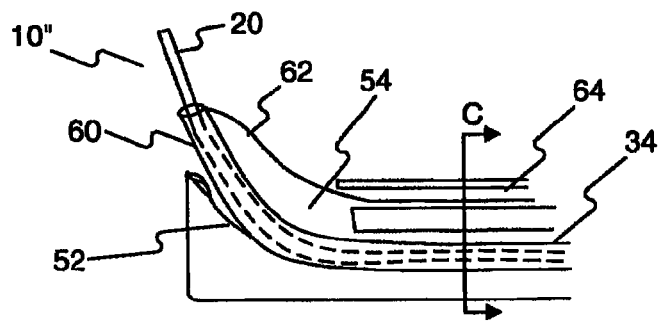
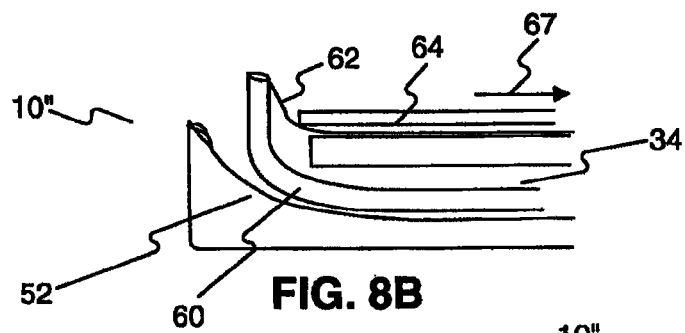
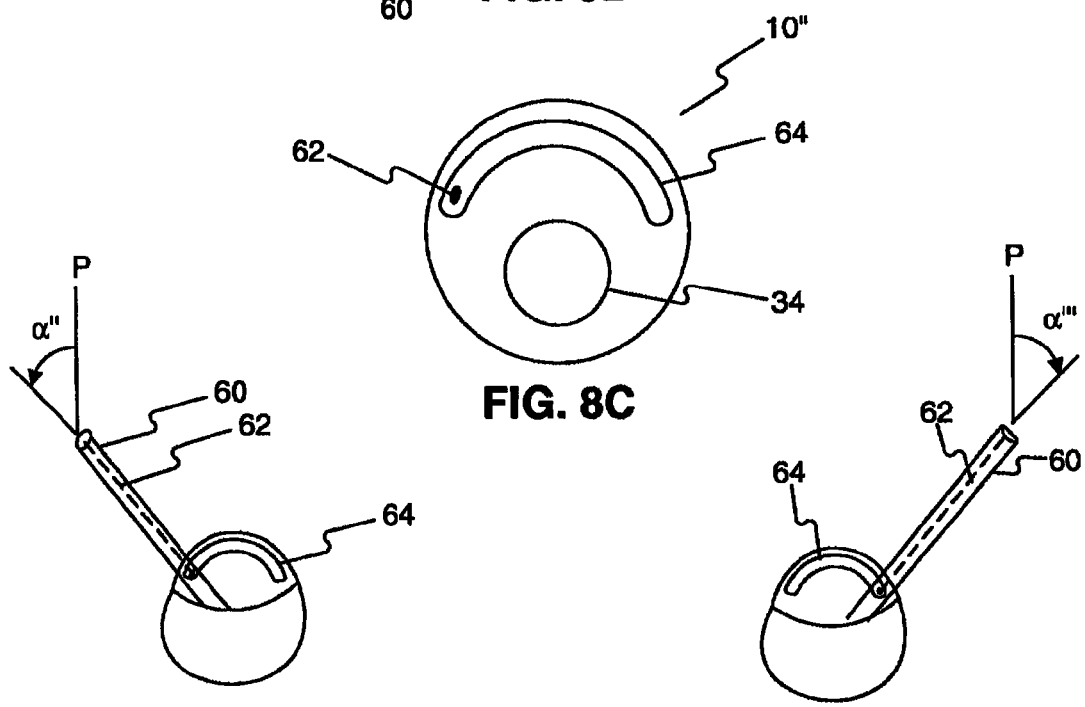

POSITIONING SYSTEM FOR MANIPULATING A CHANNEL WITHIN A MEDICAL DEVICE

CROSS-REFERENCE TO RELATED APPLICATIONS

This application is a continuation of U.S. patent application Ser. No. 12/882,719, filed on Sep. 15, 2010, which is a continuation of U.S. patent application Ser. No. 11/359,897, filed on Feb. 21, 2006, now U.S. Pat. No. 7,815,564, all of which are incorporated herein by reference in their entirety.

FIELD OF THE INVENTION

The invention relates to an endoscope system for accessing a patient's body portion and used for diagnosis and treatment of medical conditions. For example, embodiments of the invention may include a particular endoscopic positioning mechanism for placing an endoscope and an additional treatment device within desired body portions in order to assist in diagnosis and treatment of anatomical diseases and disorders.

BACKGROUND OF THE INVENTION

Endoscopes for medical use have been adopted for various diagnostic and medical treatment procedures. Endoscopes have been used for the diagnosis and treatment of a wide range of diseases and disorders that often require a physician to access the tortuous and relatively small cross-sectional areas of a patient's internal anatomical body lumens. A patient's pancreaticobiliary system (including the anatomical regions of the gall bladder, pancreas, and the biliary tree), for example, is accessed for diagnosis, and/or treatment of disorders of certain portions of the digestive system.

During treatment of the digestive system, endoscopes are often used to access and visualize a patient's pancreaticobiliary system. Once the endoscope is positioned in the desired body portion, a treatment instrument can be advanced through the working channel of the endoscope to the desired body portion. The endoscope and treatment instrument may then be manipulated as desired for visualization and treatment respectively.

Endoscopic retrograde cholangiopancreatography (ERCP) is one example of a medical procedure that uses an endoscope. ERCP enables the physician to diagnose problems in the liver, gallbladder, bile ducts, and pancreas. The liver is a large organ that, among other things, makes a liquid called bile that helps with digestion. The gallbladder is a small, pear-shaped organ that stores bile until it is needed for digestion. The bile ducts are tubes that carry bile from the liver to the gallbladder and small intestine. These ducts are sometimes called the biliary tree. The pancreas is a large gland that produces chemicals that help with digestion and hormones such as insulin.

The biliary system delivers bile produced by the liver to the duodenum where the bile assists other gastric fluids in digesting food. The biliary system includes the liver, as well as a plurality of bodily channels and organs that are disposed between the liver and the duodenum. Within the liver lobules, there are many fine "bile canals" that receive secretions from the hepatic cells. The canals of neighboring lobules unite to form larger ducts, and these converge to become the "hepatic ducts." They merge, in turn, to form the "common hepatic duct." The "common bile duct" is formed by the union of the common hepatic and the cystic ducts. It leads to the duodenum, where its exit is guarded by a sphincter muscle. This sphincter normally remains contracted until the bile is needed, so that bile collects in the common bile duct and backs up to the cystic duct. When this happens, the bile flows into the gallbladder and is stored there.

ERCP is used primarily to diagnose and treat conditions of the bile ducts, including gallstones, inflammatory strictures (scars), leaks (from trauma and surgery), and cancer. ERCP combines the use of x-rays and an endoscope. Through the endoscope, the physician can see the inside of the stomach and duodenum, and inject dyes into the ducts in the biliary tree and pancreas so they can be seen on x-rays.

An ERCP is performed primarily to identify and/or correct a problem in the bile ducts or pancreas. For example, if a gallstone is found during the exam, it can often be removed by means of a treatment instrument, eliminating the need for major surgery. If a blockage in the bile duct causes yellow jaundice or pain, it can be relieved through the use of a treatment instrument inserted through the endoscope.

Since endoscopes are often used to access the tortuous and relatively small cross-sectional areas of a patient's internal anatomical body lumens, repeated manipulation and positioning of an endoscope during a medical procedure can cause problematic side-effects. For example, repeated manipulation and positioning of the endoscope can cause unnecessary trauma to a patient's internal tissues. Improper placement and repeated attempts to access a desired treatment region can exacerbate tissue trauma as well as unnecessarily prolong the medical procedure. Accordingly, there is a need for more precise endoscope manipulation as well as manipulating an underlying treatment instrument through an access channel of an endoscope.

Thus, it is desirable to have an endoscope assembly that can more precisely access the tortuous and relatively small cross-sectional areas of certain anatomical body lumens, and more precisely manipulate a treatment device provided within an access channel of an endoscope.

SUMMARY OF THE INVENTION

Embodiments of the present invention are directed to an improved endoscope system and a positioning device for manipulating a treatment device that obviates one or more of the limitations and disadvantages of prior medical devices.

In one embodiment, a medical device comprises an elongated flexible tube including a distal end and a proximal end. The tube defines a longitudinal axis and a channel extending from the proximal end to an aperture at the distal end. A positioning mechanism is positionable at the distal end of the flexible tube proximate the aperture and configured for rotation relative to the longitudinal axis of the flexible tube and lateral deflection at and relative to the distal end of the flexible tube to control a direction at which a treatment instrument extends from the aperture.

In various embodiments, the device may include one or more of the following additional features: wherein a distal portion of the positioning mechanism is housed within a recess at the distal end of the flexible tube, the positioning mechanism being configured for rotation about a pin within the recess; wherein the positioning mechanism comprises a tube housed within the channel; wherein a distal portion of the positioning mechanism is configured for lateral deflection through actuation of a pull wire connected to the positioning mechanism and extending proximally within the elongated flexible tube; wherein a distal portion of the positioning mechanism is connected to the flexible tube by at least one spring, the distal portion of the positioning mechanism being configured for lateral deflection upon movement of a wedge between the flexible tube and the distal portion of the positioning mechanism; wherein a living hinge separates a distal portion of the positioning mechanism from a remaining portion of the positioning mechanism; wherein a pin extends through the distal portion of the positioning mechanism and a distal portion of the tube housed within the channel; wherein the aperture is a side facing aperture opening laterally along the flexible tube; wherein the positioning mechanism is configured for movement through at least two degrees of freedom; wherein the positioning mechanism is configured for movement through at least three degrees of freedom; wherein the positioning mechanism is rotatable about two axes; wherein the positioning mechanism is configured for rotating a treatment instrument extended through the aperture relative to the longitudinal axis of the flexible tube; wherein the medical device is an endoscope that includes visualization components therein; wherein the medical device is an endoscope that includes illumination components therein; wherein the medical device is an endoscope that includes an additional positioning mechanism for controlled deflection of the elongated flexible tube; wherein the positioning mechanism comprises a sleeve configured to receive a treatment instrument therein, the sleeve being slidably housed and rotatable within the channel and having a distal end extendable beyond the aperture; further comprising a deflection control mechanism connected to a distal end of the sleeve and moveable longitudinally and laterally within and relative to the flexible tube such that the distal end of the sleeve deflects relative to the flexible tube; wherein the deflection control mechanism comprises a pull wire connected to a distal end of the sleeve and housed within a pull wire lumen within the flexible tube; wherein the pull wire lumen exhibits an arc shape configured to allow the pull wire to be rotated from one end of the arc shaped lumen to another; wherein the sleeve is configured for movement through at least two degrees of freedom; wherein the sleeve is rotatable about two orthogonal axes; wherein the sleeve is configured for movement through at least three degrees of freedom; wherein the sleeve is configured for selectively rotating a treatment instrument extended therein and beyond the aperture through a predetermined angle relative to the longitudinal axis of the flexible tube; further comprising a handle at the proximal end of the flexible tube, the handle including a control mechanism connected to a proximal end of the positioning mechanism configured for rotating the positioning mechanism within the channel of the flexible tube; wherein the control mechanism comprises a cylindrical rotation post extending from a rotation ring, the rotation ring being connected to a proximal end of the positioning mechanism; and wherein the control mechanism of the handle includes a locking mechanism for fixing the orientation of the positioning mechanism within the channel of the flexible tube.

Another embodiment is directed to a method of positioning a treatment instrument in a body comprising, providing a medical device comprised of an elongated flexible tube including a distal end and a proximal end. The tube defines a longitudinal axis and a channel extending from the proximal end to an aperture at the distal end. A positioning mechanism is positionable at the distal end of the flexible tube proximate the aperture and configured for rotation relative to the longitudinal axis of the flexible tube and lateral deflection at and relative to the distal end of the flexible tube to control a direction at which a treatment instrument extends from the aperture. The method includes inserting the medical device into an anatomical lumen of the body, inserting a treatment instrument through the channel, positioning the treatment instrument by rotating the positioning mechanism relative to the working channel of the flexible tube, and positioning the treatment instrument by laterally deflecting a distal portion of the positioning mechanism.

In various embodiments, the method may include one or more of the following additional features: further comprising extending the treatment instrument beyond the aperture of the flexible tube and into the anatomical lumen; further comprising retracting the treatment instrument into the medical device, repositioning the medical device within the anatomical lumen, applying torque to the positioning mechanism to rotate the treatment instrument housed therein, and extending the treatment instrument through the aperture; wherein the treatment instrument is positioned within a bile duct during an ERCP procedure; wherein the positioning mechanism is rotated 180 degrees relative to the longitudinal axis of the flexible tube; wherein a distal portion of the positioning mechanism is housed within a recess at the distal end of the flexible tube, and the distal portion of the positioning mechanism is rotated about a pin within the recess; wherein the positioning mechanism comprises a tube housed within the channel and a distal portion of the positioning mechanism is laterally deflected through actuation of a pull wire connected to the positioning mechanism and extending proximally within the elongated flexible tube; wherein a pin extends through the distal portion of the positioning mechanism and a distal portion of the tube housed within the channel; wherein the positioning mechanism comprises a sleeve configured to receive a treatment instrument therein, the sleeve being slidably housed and rotatable within the channel and having a distal end extendable beyond the aperture; further comprising a deflection control mechanism connected to a distal end of the sleeve and moveable longitudinally and laterally within and relative to the flexible tube such that the distal end of the sleeve deflects relative to the flexible tube; and wherein the deflection control mechanism comprises a pull wire and wherein deflection of the sleeve is controlled by proximal actuation of the pull wire.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIGS. 5A and 5B are front views of a distal part of an endoscope according to an embodiment of the present invention.

FIG. 6 is a side view of a distal part of an endoscope according to an embodiment of the present invention.

FIGS. 8A and 8B are cross-sectional views of a distal portion of an endoscope according to another embodiment of the present invention.

FIG. 8C is a cross-sectional view of an endoscope taken along line C-C in FIG. 8A.

FIGS. 9A and 9B are front views of a distal part of an endoscope according to another embodiment of the present invention.

DESCRIPTION OF THE EMBODIMENTS

Figure 1:
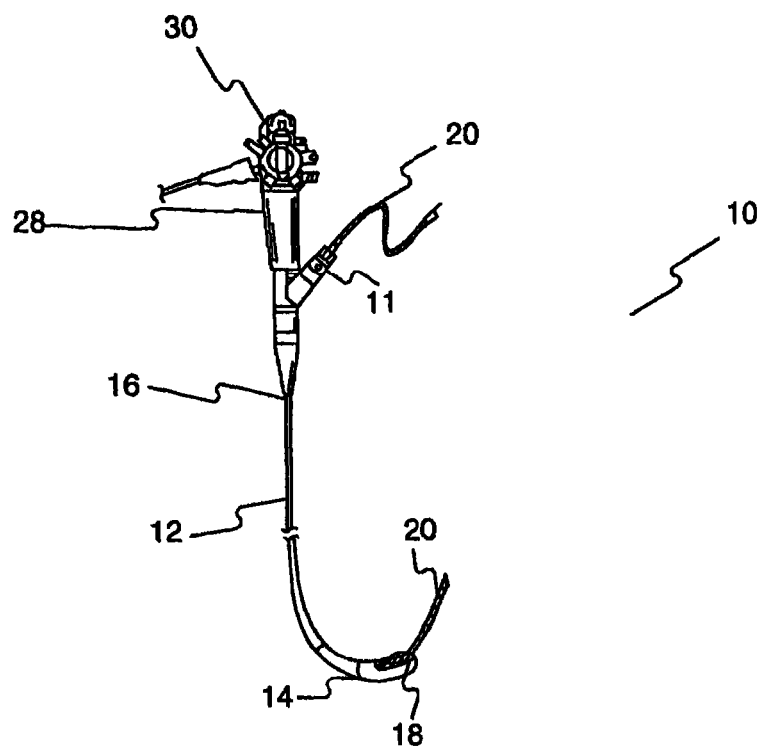
FIG. 1 is a perspective view of a prior art endoscope system.

Reference will now be made in detail to the exemplary embodiments of the invention, examples of which are illustrated in the accompanying drawings. Wherever possible, the same reference numbers will be used throughout the drawings to refer to the same or like parts. The drawing figures of this application are intended to provide a general understanding of the working elements of the underlying system. Accordingly, unless explicitly stated, the figures do not represent a literal depiction of proportional dimensions or the precise locations for the illustrated inter-related components.

According to exemplary embodiments, the invention relates to a medical device for positioning a treatment device and/or viewing a patient's internal body portion. In embodiments that use a treatment device in an endoscopic medical procedure, the treatment device can be advanced through a working channel of an endoscope, including an endoscope specifically designed and/or sized for use with the treatment device, and into a tissue tract. For purposes of this disclosure, "treatment device" or "treatment instrument" includes, for example, any medical device advanced through a working channel of an endoscope and for use during an endoscopic procedure. Exemplary treatment instruments include, but are not limited to, guide wires, cutting or grasping forceps, biopsy devices, snare loops, injection needles, cutting blades, scissors, retractable baskets, retrieval devices, ablation and/or electrophysiology catheters, stent placement devices, surgical stapling devices, and balloon catheters.

FIG. 1 illustrates a known endoscope system. For purposes of this disclosure, "distal" refers to the end further from the device operator during use and "proximal" refers to the end closer to the device operator during use. FIG. 1 depicts an endoscope 10 including a flexible outer tube 12 extending between a distal end 14 and a proximal end 16 of the device. Endoscope 10 includes a treatment device insertion port 11 for receiving a treatment device 20 into a working channel of the endoscope 10. The distal end 14 of the endoscope system 10 includes a side facing operation window 18 that can include visualization and lighting components for viewing during a treatment procedure. In addition, a working channel (not shown) extends within the endoscope 10 and terminates at the operation window 18, thereby allowing the treatment instrument 20 to be extended from the distal end of the endoscope 10. The extension of the treatment instrument 20 at a desired treatment site can be then viewed through the visualization components, which transmit images to the proximal end of the endoscope 10, as known in the art. While FIG. 1 illustrates a side facing operation window 18, both front/forward facing and oblique/intermediate angled windows are known.

Figure 2:
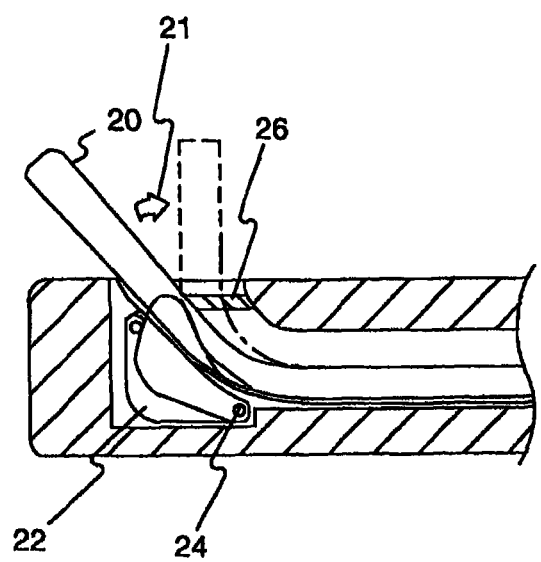
FIG. 2 is a cross-sectional view illustrating the structure of a known elevator device.

FIG. 2 illustrates a cross-sectional view of a distal portion of a known endoscope system including a deflecting lever/elevator device for deflecting a treatment instrument as the instrument is extended beyond a working channel of an endoscope. As seen in FIG. 2, a deflecting lever 22 is rotated clockwise about a pin 24 by means of a pull wire 26 connected to an upper portion of the deflecting lever 22. Upon actuation of the pull wire 26 through proximal movement thereof, the deflecting lever 22 deflects the treatment device 20 in order to alter the angle at which the treatment device 20 exits the endoscope's working channel, resulting in the position of device 20 shown by the dashed lines in FIG. 2. Accordingly, arrow 21 depicts "lateral deflection" of device 20 relative to the underlying endoscope body. By means of pull wire 26, the endoscope operator can control the placement of the treatment instrument 20 as it is positioned during a medical procedure.

As seen in FIG. 1, a handle 28 at the proximal end 16 of the device can include various positioning controls 30 to effectuate bending and rotation of the flexible outer tube 12 for positioning of the device during a medical procedure. In addition, the handle can include a distinct positioning control for actuation of the deflection lever pull wire 26. During a medical procedure such as, for example, an ERCP procedure, the treatment instrument 20 must be precisely inserted into a particular duct in the biliary tree. While the use of a deflection lever 26 is capable of altering the angle at which the treatment device exits the endoscope, precise positioning often requires repeated manipulation of the distal end of the endoscope including the operation window in order to achieve proper placement of the treatment device 20. As noted above, this repeated manipulation of the underlying endoscope 10 can lead to tissue trauma and unnecessarily prolong the entire medical procedure.

As seen in the embodiment of FIG. 2, the deflection lever 26 is displaceable about a single axis (i.e. the axis coincident with the pin 24). Accordingly, lever 26 is movable about and only effectuates movement of the treatment device 20 through one degree of freedom. Precise manipulation of a treatment instrument is increased when manipulation is afforded along or about an additional particular coordinate axis. A degree of freedom describes flexibility of motion added due to displacement along or about a particular coordinate axis.

Figure 3:
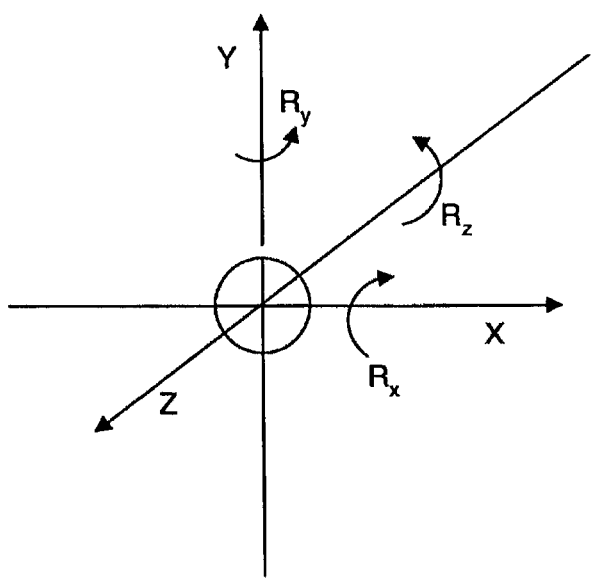
FIG. 3 illustrates an exemplary coordinate system for designating translational and rotational displacement of elements in a system of connected bodies.

FIG. 3 illustrates a known Cartesian coordinate system illustrating the three orthogonal axes of X, Y, and Z. A linkage or any system of connected bodies that has complete freedom of motion (even if only in a limited area) has six degrees of freedom. Three modes are translation (i.e. the ability to move in each of three dimensions in a direction parallel to each of the three orthogonal axes). An additional three modes are rotation, i.e. the ability to change an angular position around the three orthogonal axes. Only three degrees of freedom are necessary to move a structure anywhere in space, but additional degrees of freedom provide more versatility. For example, each of the following is one degree of freedom: moving up and down along the Y axis (heaving); moving left and right along the X axis (swaying); moving forward and back along the Z axis (surging); tilting up and down (rotation Rx about the X axis); turning left and right (rotation Ry about the Y axis); and tilting side to side (rotation Rz about the Z axis). Accordingly, a positioning mechanism that effectuates movement through more than one degree of freedom will allow for more precise positioning of an underlying treatment device.

Figure 4A:
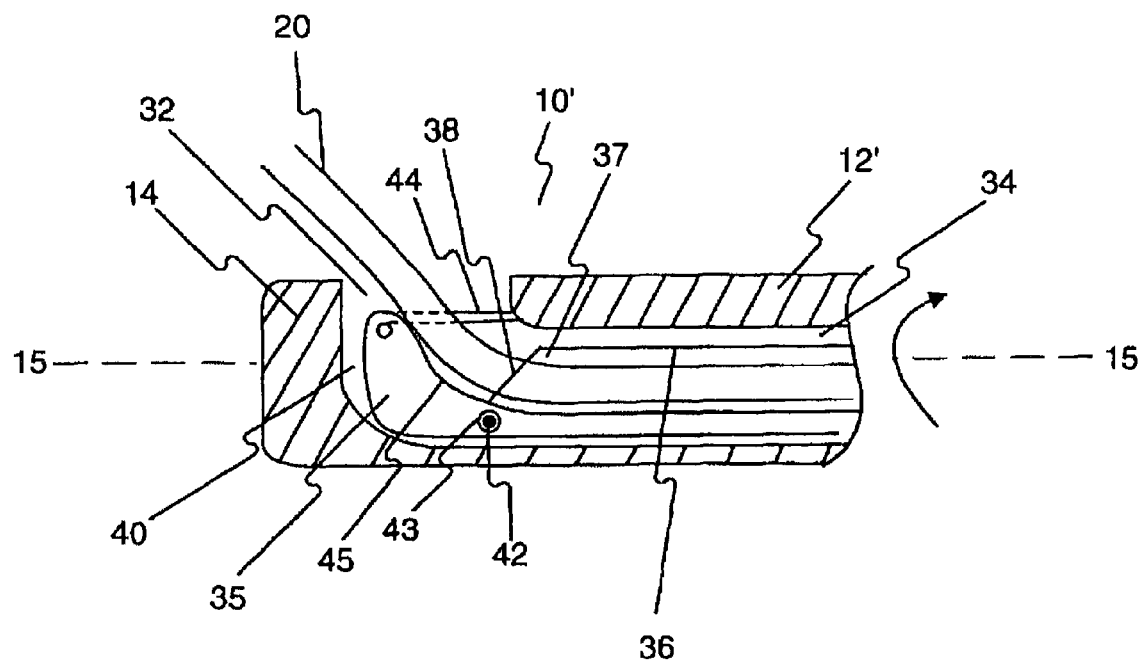
FIG. 4A is a cross-sectional view of a distal portion of an endoscope according to an embodiment of the present invention.

FIG. 4A depicts a cross-sectional view of a distal end 14 of an improved endoscope 10'. The distal portion of endoscope 10' includes an exterior flexible outer tube 12', a side facing operation window aperture 32, and a working channel 34 forming a lumen within the endoscope 10' and extending from the proximal end of the endoscope 10' and terminating at the operation window aperture 32. The flexible outer tube 12' extends along a longitudinal axis 15. The working channel 34 extends proximally through the endoscope 10' to a proximal working channel access port through which a treatment instrument can be tracked.

In addition, working channel 34 houses a separate torqueable flexible tube 36 configured for rotation within channel 34 and about the longitudinal axis 15. Tube 36 can be formed, for example, from any known material suitable for use in medical procedures. For example, polymer materials commonly used in medical device components are suitable for providing a flexible, torqueable, component body. Alternatively, tube 36 could be formed as a metal coil or braid or as a composite structure of a polymer tube and metal coil or braid. Such an alternative structure may exhibit enhanced properties for transmitting torque relative to structure comprised of polymer alone.

Tube 36 is housed and extends proximally within the working channel 34. Tube 36 is configured to freely rotate within the working channel 34 relative to the flexible outer tube 12'. In addition, the tube 36 is sized to accommodate one or more treatment instruments therein for effectuating positioning and placement of a treatment instrument during a medical procedure. In order to facilitate the rotation of tube 36 within the working channel 34, a portion of the outer surface of tube 36 may be formed (or coated) with a thin layer of a lubricious polymer material, such as for example, polytetrafluoroethylene (PTFE). A layer of polymer material along the outer surface of tube 36 provides a low friction surface for contact with the corresponding internal surface of working channel 34. The lower friction surface reduces the potential for any resistance to free rotation of tube 36. Additionally, or as an alternative, friction can also be lowered by use of known lubricants such as silicone oil, for example.

An additional thin layer of a lubricious polymer material may be coated along the inner surface of the working channel 34 to prevent galling of the contacting surfaces during movement of tube 36 relative to channel 34 during use. The tube 36 extends distally within channel 34 terminating at a distal opening 38 just proximal to the operation window aperture 32. In addition, the tube 36 may be sized to accommodate visualization components (not shown), such as, for example, fiber optics housed within endoscope 10' for viewing an internal treatment site during a medical procedure.

A deflection elevator 35 is housed within a recess 40 at the distal end of the endoscope 10' at a position opposite the operation window aperture 32. The elevator 35 is positioned for controlled lateral deflection/rotation within the recess 40, for example, through rotation about the axis of a pin 42 extending laterally through a pin aperture 43 in elevator 35. The elevator 35 may include a curved concave surface 45 (also see FIG. 7) configured to maintain contact with a treatment instrument 20 extended beyond the opening 38 of tube 36. The curved surface 45 of the elevator 35 acts as the surface for transferring a deflection force against a treatment instrument 20 during extension of the treatment instrument 20 through the endoscope 10'. As seen in FIG. 4A, rotation of elevator 35 about pin 42 can be effectuated through proximal actuation of a pull wire 44 connected to an upper portion of the elevator 35. Since the pin 42 is not connected to the flexible tube 12', the generation of a moment about the axis of pin 42 in order to deflect elevator 35 may require that the tube 36 be fixed in position relative to the flexible tube 12'. When tube 36 is fixed relative to the flexible tube 12', the proximal actuation of pull wire 44 effectuates rotational displacement of elevator 35 about the axis of pin 42 rather than the proximal displacement of tube 36 within working channel 34.

Accordingly, when tube 36 is fixed relative to outer tube 12', proximal actuation of pull wire 44 generates a moment about the pin 42 thereby effectuating controlled deflection of elevator 35. During use, controlled deflection of elevator 35 changes the angle at which a treatment instrument 20 exits endoscope 10' through aperture 32, as shown in FIG. 6, for example. Additionally, or alternatively, the distal end of elevator 35 can be arranged to also deflect at an angle side to side relative to the longitudinal axis of tube 36 within the recess 40. In other words, the distal end of elevator 35 can be configured for rotation in a direction in and out of the page with regard to FIG. 4A (i.e. moving the distal end of elevator 35 in the direction of Ry about the Y axis as depicted in FIG. 3). This rotation can be arranged, for example, through a dual pull wire configuration controlling the side to side deflection of the distal end of elevator 35 relative to the distal end of the tube 36.

The elevator 35 is connected to a distal portion of lumen 36 such that any rotation of lumen 36 relative to the longitudinal axis 15 also effectuates rotation of elevator 35 about axis 15. Elevator 35 and lumen 36 can be integrally formed as a single component. For example, the elevator 35 and lumen 36 can be formed through a molding process resulting in a single component. Alternatively, elevator 35 and lumen 36 can be connected through any known method for connecting working elements of an endoscopic system. One connection, for example, illustrated in FIG. 4A, depicts pin 42 extending through both elevator 35 and a distal portion of lumen 36. Accordingly, in the illustrated embodiment, pin 42 serves as the axis about which elevator 35 rotates to transmit deflection to a treatment instrument 20 and also serves as the element through which elevator 35 and lumen 36 are connected. In order to assure a reliable connection, a portion of lumen 36 at the distal end of lumen 36 can be provided with a solid mounting block portion through which pin 42 can extend. Such a solid mounting block for receiving pin 42 increases the amount of surface area through which torque is transferred from the proximal end of lumen 36 to elevator 35.

Figure 4B:
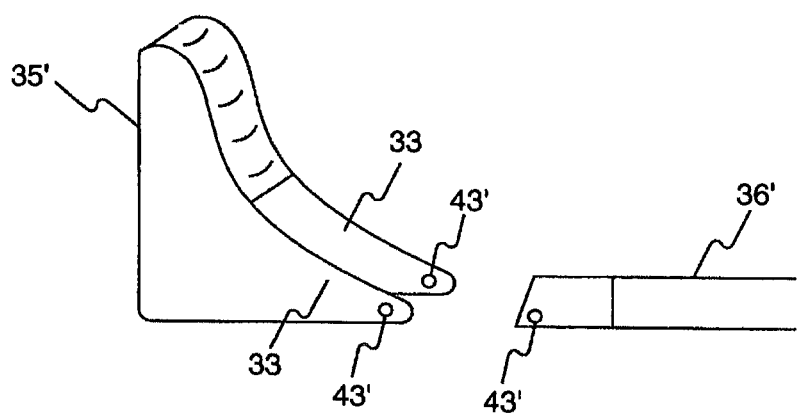
FIG. 4B illustrates an alternative elevator arrangement at a distal portion of an endoscope according to an embodiment of the present invention.

As another example, the connection of elevator 35 and lumen 36 could be completed through an arrangement as depicted in FIG. 4B. FIG. 4B illustrates a disassembled arrangement of an elevator 35' and lumen 36'. The arrangement of FIG. 4B is similar to elevator 35 and lumen 36 except that the previously described mounting block arrangement has been replaced with dual side arm posts 33 each having a pin aperture 43' through which pin 42 extends after assembly. In addition, the distal end of lumen 36' could be capped with a thin walled metal tube. This metal tube would have the strength to support its own aperture 43' for receiving pin 42. Just as in FIG. 4A, in FIG. 4B, pin 42 extends through the elevator 35' and lumen 36' thereby connecting the two and allowing lateral deflection of the elevator 35' relative to the lumen 36'.

Figure 4C:
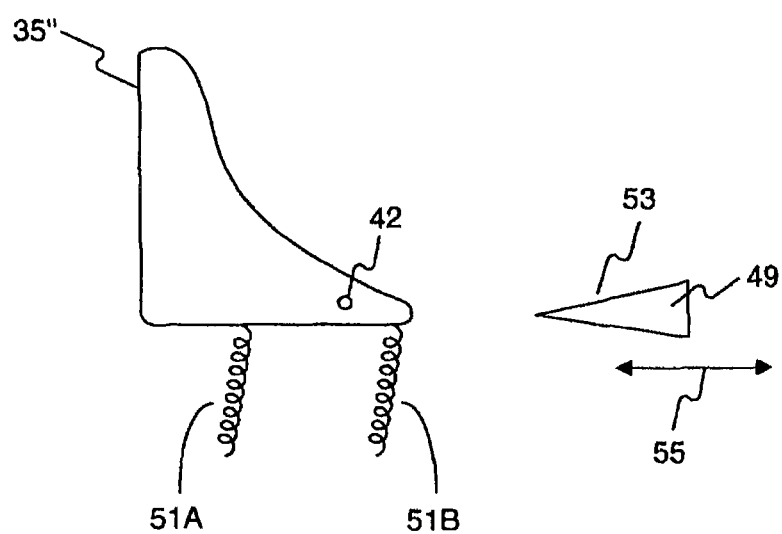
FIG. 4C illustrates an alternative elevator arrangement at a distal portion of an endoscope according to an embodiment of the present invention.

As another example, instead of using a pull wire 44, deflection control of an elevator can be provided through an arrangement combining at least one spring and a wedge element. FIG. 4C depicts an arrangement of an elevator 35" and a wedge 49. For example, elevator 35" can be connected within a recess 40 (see, e.g., FIG. 4A) at a distal end of an endoscope by a distal spring 51A and a proximal spring 51B. A wedge 49 having a ramp 53 can be provided and configured for longitudinal movement in the direction of arrow 55 underneath an elevator 35". Upon forward movement of the wedge 49 underneath the elevator 35", contact between the surface of ramp 53 and the underside of elevator 35" results in a lateral deflection of the elevator 35" about pin 42. Springs 51A and 51B of a predetermined force constant are positioned such that the controlled longitudinal displacement of wedge 49 provides an alternative system for providing lateral deflection.

As yet another example, the device of FIG. 4A could work without a pin 42. The elevator 35 could be rigidly attached to the lumen 36. A living hinge feature could be incorporated into the structure of the elevator 35 in the location where the pin is depicted in FIG. 4A. Living hinges are thin sections of material that connect two segments of a part to keep them together and allow one part to be repeatedly moved relative to another, such as, for example, the hinge arrangement in a plastic toolbox. This living hinge would be a discrete thin section in the elevator structure designed so that the elevator would bend at that location.

As noted above, elevator 35 is configured for clockwise rotation about pin 42 through actuation of pull wire 44. Pull wire 44 is connected at an upward offset distal position along the elevator 35 such that proximal movement of pull wire 44 rotates the elevator 35 about rotation pin 42. The pull wire 44 extends proximally within a pull wire channel (not shown) of the endoscope 10' where it extends for connection with a positioning control device at a handle at the endoscope's proximal end. As pull wire 44 is displaced in a proximal direction, the elevator 35, and in turn a treatment instrument 20, are rotated such that the angle at which treatment instrument 20 extends from the endoscope 10' is increased.

Pull wire 44, for example, can extend for connection to a bending lever or rotation wheel control device where proximal actuation can be effected by an operator. While a pull wire element is illustrated as the mechanism for deflection of the elevator 35, alternative deflection mechanisms can be used, including, but not limited to, forward acting push wires, or stylets, electronic piezoelectric bending transducers, electroactive polymers, shape memory materials, and an inflatable cuff element underlying the elevator 35.

Figure 4D:
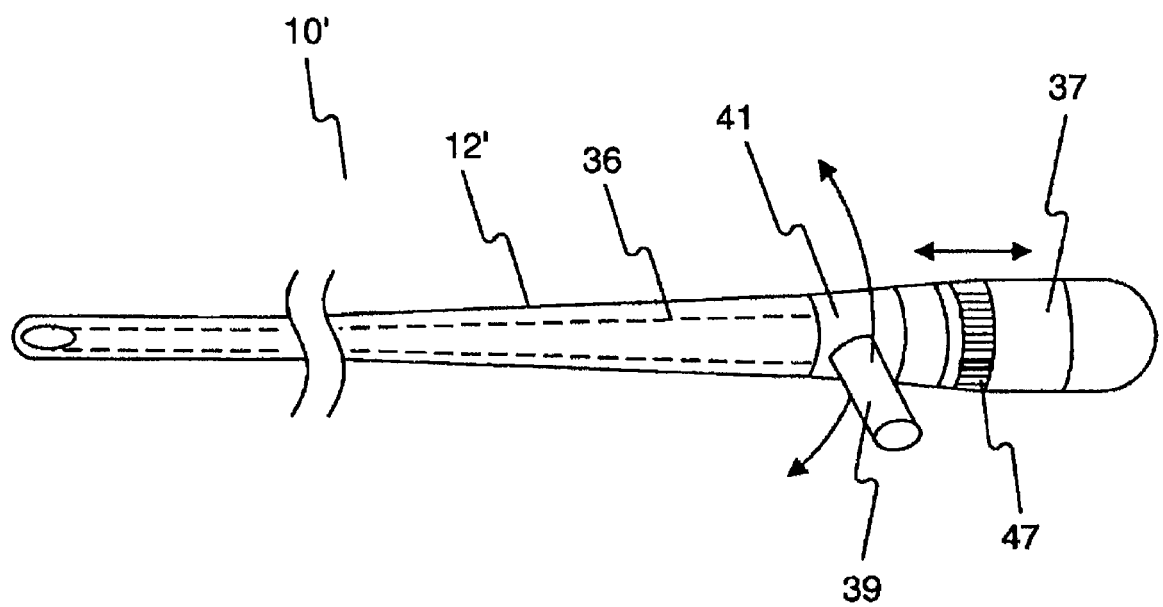
FIG. 4D illustrates a proximal portion of an endoscope according to an embodiment of the present invention.

FIG. 4D, for example, depicts one embodiment for a handle 37 provided at the proximal end of the endoscope 10'. As seen in FIG. 4D, the flexible outer tube 12' extends proximally to a handle 37. Handle 37 may include a cylindrical rotation post 39 extending from a rotation ring 41. The ring 41 is rotatably connected to a proximal end of tube 36 such that rotation of post 39 and ring 41 effectuates rotation of tube 36 within the working channel 34 of the endoscope 10'. In addition, the rotation ring 41 can incorporate a locking mechanism for releasably fixing the rotational and longitudinal position of tube 36 relative to the working channel 34. Exemplary locking mechanisms include, but are not limited to, a constricting rubber grommet mechanism, a ratchet, a thumbscrew, a button, and an extendable pin and receiving aperture arrangement configured for mating engagement along a proximal end of the tube 36. Alternatively, the operator can simply maintain the position of tube 36 relative to the working channel 34 by hand.

Handle 37 also comprises a deflection control slide ring 47 connected to a proximal portion of the pull wire 44. As seen in FIG. 4D, the slide ring 47 extends back and forth along a slide channel formed along the exterior of the handle 37. Distal and proximal movement of slide ring 47 relative to the exterior surface of the handle 37, effectuates distal and proximal movement of the pull wire 44, which actuates deflection of elevator 35, as seen in FIG. 4A. Accordingly, upon proper orientation of tube 36, an operator can fix the position of tube 36 relative to the working channel 34 and commence deflection of elevator 35 as desired.

While a slide ring and rotation post arrangement is illustrated, alternative handle positioning configurations are also contemplated. For example, the pull wire 44 can be extended and retracted by a worm gear arrangement, a rack and pinion arrangement, a lever, a typical rotation knob on an endoscope, through electronic means, or any alternative mechanism for effectuating longitudinal displacement of an elongated component.

Because tube 36 is configured for rotation about the longitudinal axis 15 of the endoscope 10', and elevator 35 is configured for controlled rotation about the axis of pin 42, endoscope 10' is capable of displacing a treatment instrument 20 through at least two degrees of freedom. FIGS. 5A and 5B, for example, illustrate a degree of freedom permitting rotation of a treatment instrument 20 within the working channel 34 of the underlying endoscope 10'. Referring to FIGS. 5A and 5B, an exemplary range of rotation for tube 36, elevator 35, and a treatment instrument 20 associated therewith is illustrated. FIG. 5A is a front view of endoscope 10' depicting the counter-clockwise (viewing from the distal end) rotation of tube 36 within the endoscope 10'. Rotation of tube 36 is transferred into rotation of elevator 35, and in turn effectuates rotation of treatment instrument 20. FIG. 5A illustrates rotation of elevator 35 through an angle α of about 55 degrees relative to a vertical plane P bisecting the endoscope 10' in FIG. 5A. Conversely, FIG. 5B illustrates a front view of endoscope 10' depicting the clockwise (viewing from the distal end) rotation of tube 36 within the endoscope 10'. In FIG. 5B, rotation of elevator 35 in a direction opposite that of FIG. 5A is depicted through an angle α' of about 55 degrees relative to a vertical plane bisecting the endoscope 10'. While a combined angular rotation of 110 degrees is illustrated, alternative rotational ranges are possible and the example of 110 degrees is not intended to be limiting. The overall range of rotation for tube 36 and elevator 35 may be limited by the configuration of the boundary of aperture 32, which houses the elevator 35. For example, as seen in FIGS. 5A and 5B, treatment instrument 20 can be rotated relative to the outer flexible tube 12' of the endoscope 10' only until an exterior side surface of treatment instrument 20 comes in contact with the boundary of aperture 32.

FIG. 6 depicts a side view of the distal portion of endoscope 10' and, in particular, the deflection of a treatment instrument 20 through an additional degree of freedom from that illustrated in FIGS. 5A-5B. Actuation of deflection pull wire 44, illustrated in part in dashed lines in FIG. 6, causes rotation of elevator 35 in order to increase or decrease the deflection angle β at which the treatment instrument 20 extends from the working channel of underlying endoscope 10'. As noted above, the generation of a moment about the axis of pin 42 in order to deflect elevator 35 may require that the tube 36 be fixed in position relative to the flexible tube 12'. When tube 36 is fixed relative to the flexible tube 12', the proximal actuation of pull wire 44 effectuates rotation of elevator 35 about pin 42 and causes lateral deflection of treatment instrument 20 between an angle of about 30 degrees to about 135 degrees relative to the longitudinal axis 15 of the endoscope 10'.

Figure 7:
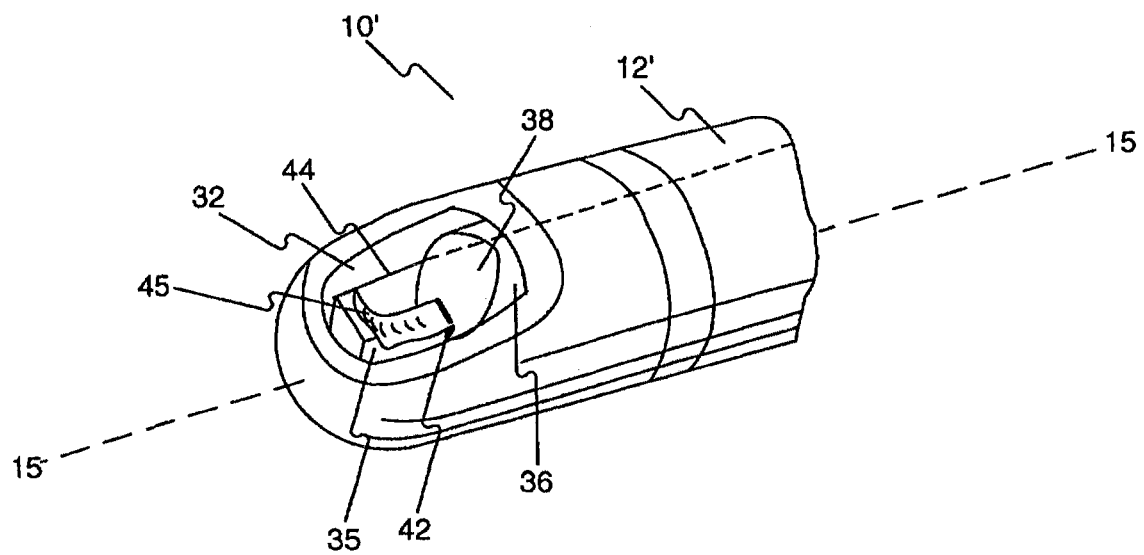
FIG. 7 is a perspective view of a distal part of an endoscope according to an embodiment of the present invention.

FIG. 7 is a perspective view of a distal part of an endoscope 10'. FIG. 7 depicts a distal portion of an endoscope 10' including an aperture 32 leading to a recess that houses elevator 35. Elevator 35 can be manipulated through two distinct degrees of freedom in order to more precisely position a treatment instrument within an endoscope. As noted above, one degree of freedom is permitted through rotation of elevator 35 about the axis of pin 42, while another separate degree of freedom is permitted through rotation of lumen 36 relative to longitudinal axis 15.

FIGS. 8A-9B illustrate another embodiment for effectuating more precise manipulation of a treatment instrument within a working lumen of an endoscope. FIG. 8A depicts an arrangement of a distal portion of an endoscope 10" including a positioning mechanism for manipulation of a treatment instrument 20. In FIG. 8A, a treatment instrument 20 is inserted within an extendable sleeve 60 housed within the working channel 34 that extends through endoscope 10". Slidable sleeve 60 extends within the channel 34 and is configured for movement relative to the channel 34. Sleeve 60 can be extended back and forth through working channel 34 where, in side facing operation window embodiments, a ramp 52 leads to the exterior of the endoscope 10" through a side port aperture 54.

A sleeve deflection pull wire 62 connects to a distal end of the sleeve 60 and extends proximally through a pull wire lumen 64 within the flexible tube 12'. The sleeve 60 may be configured to exhibit a predetermined level of rigidity such that a treatment instrument 20 extended therethrough will be reliably directed coincident with the direction sleeve 60 extends from the working channel 34. For example, during a treatment procedure, sleeve 60 can be used to position the point in space at which the distal end of a treatment instrument 20 is located within a patient's body. This further positioning adjustment mechanism is advantageous in that the distal end of a treatment instrument 20 can be precisely located without requiring repeated manipulation and trauma-causing movement of the entire underlying endoscope body. If the extended sleeve 60 is easily deflected and collapsible during contact with internal body tissues, proper control and repeatable placement of sleeve 60 (and in turn the treatment instrument 20 extended therethrough) may not be possible.

FIG. 8B depicts sleeve 60 extended outside the working channel 34 of endoscope 10". FIG. 8B also depicts controlled deflection of sleeve 60 through proximal actuation of pull wire 62 in the direction of arrow 67. Proximal displacement of pull wire 62 draws the distal end of sleeve 60 closer to the distal opening of pull wire lumen 64. Therefore, precise control of the angle at which sleeve 60 extends outside the working channel 34 is effectuated through manipulation of pull wire 62. During use, an operator may control the placement of a treatment instrument 20 by extending the sleeve 60 to a desired position and then selectively actuating pull wire 62 while fixing the longitudinal position of the proximal portion of sleeve 60 within the working channel 34. Therefore, the distal orientation of the sleeve 60 can be selectively manipulated without effecting displacement of any portion of sleeve housed within channel 34.

FIG. 8C depicts a cross-sectional view through endoscope 10" taken along line C-C in FIG. 8A. As seen in FIG. 8C, pull wire lumen 64 may be formed in an arc shape which allows for angular displacement of the pull wire 62 through a predetermined angle corresponding to the size of the arc-shaped lumen 64. For example, during a medical procedure, sleeve 60 may be rotated within the channel 34. After rotation of a sleeve 60 relative to channel 34, actuation of pull wire 62 will effectuate bending of sleeve 60 at only one angular orientation unless pull wire 62 is also free to move laterally relative to the exterior surface of endoscope 10". In the illustrated embodiment this lateral movement is accomplished by lateral movement of the pull wire 62 within the lumen 64, for example, by movement of the pull wire from one end lateral end of the lumen 64 to another. While the lumen 64 is illustrated as having an arc shape, alternative shapes are possible, so long as lateral movement of pull wire 62 is permitted.

Through the arrangement depicted in FIG. 8C, lumen 64 is shaped to house pull wire 62 throughout a predetermined angular displacement, such as, for example, a range of 180 degrees. In addition, in is contemplated that angular displacement may include a range of up to 360 degrees. Accordingly, upon combined rotation of sleeve 60, lateral movement of pull wire 62, and proximal deflection of pull wire within lumen 64, sleeve 60 can be deflected through a range of angular orientation relative to the longitudinal axis 15 of endoscope 10".

FIGS. 9A and 9B depict the controlled displacement of sleeve 60 through three degrees of freedom, i.e. one controlling a degree of lateral deflection as sleeve 60 extends from the endoscope 10", another controlling the angular orientation, or rotation of sleeve 60 relative to the longitudinal axis of endoscope 10", and another controlling the distance sleeve 60 extends beyond the working channel 34.

FIG. 9A for example, illustrates a front view of endoscope 10" depicting the counter-clockwise (viewing from the distal end) rotation of sleeve 60 and pull wire 62 within the endoscope 10". Rotation of sleeve 60 and pull wire 62 is depicted through an angle $\alpha''$ of about 55 degrees relative to a vertical plane P bisecting the endoscope 10". Conversely, FIG. 9B illustrates a front view of endoscope 10' depicting the clockwise (viewing from the distal end) rotation of sleeve 60 and pull wire 62 within the endoscope 10". In FIG. 9B, the sleeve 60 and pull wire 62 are rotated in a direction opposite that of FIG. 9A and depicted as rotated through an angle $\alpha'''$ of about 55 degrees relative to vertical plane P bisecting the endoscope 10". While a combined angular rotation of about 110 degrees is illustrated, alternative ranges of rotation are possible and the example of 110 degrees is not intended to be limiting.

It is contemplated that all of the embodiments disclosed herein may include manipulating pull wires similar to pull wire 62 illustrated in FIGS. 8A-9B. For example, each of the treatment device 20, tube 36, and sleeve 60 can be arranged to include up to four pull wires to add two or more additional degrees of freedom to the tip of the endoscopic positioning system described herein. In addition, it is contemplated that any of treatment device 20, tube 36, sleeve 60, and elevators 35 and 35' may be incorporated with a return spring element for resiliently biasing the associated element toward a "home" position.

Figure 10:
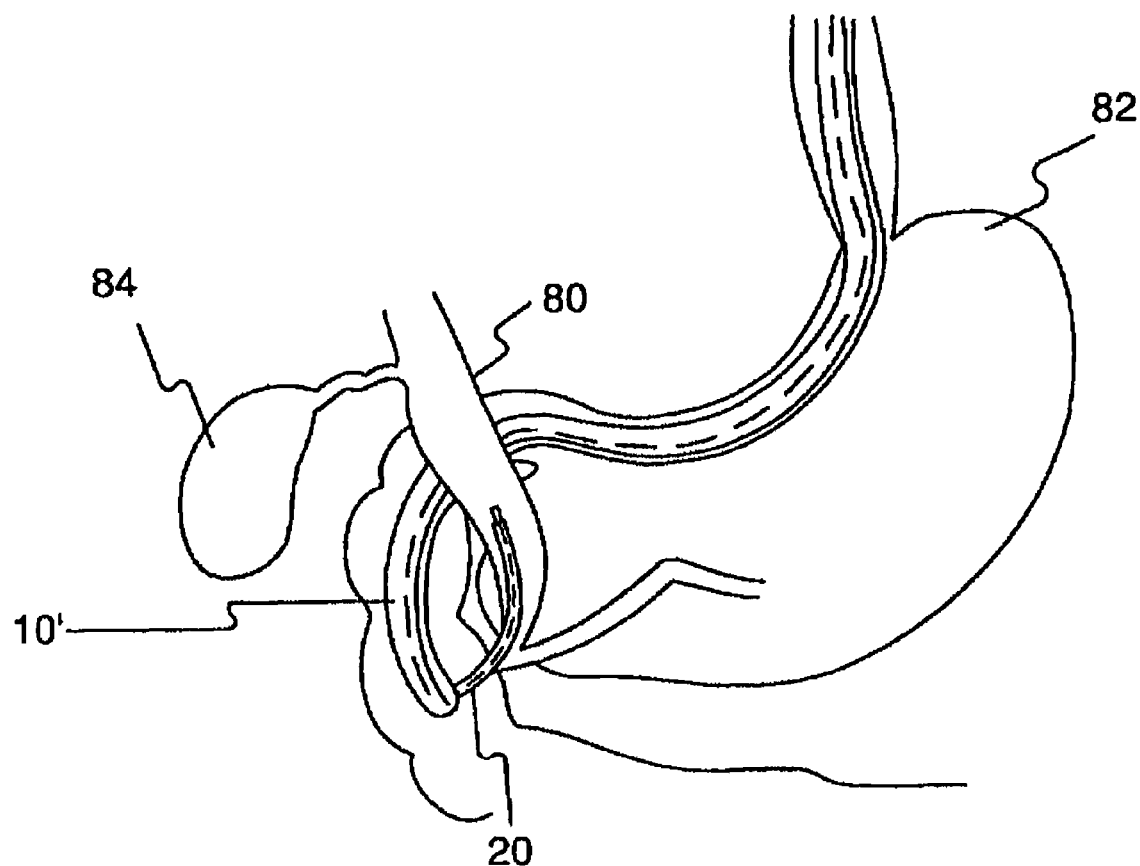
FIG. 10 illustrates the positioning of an endoscope and treatment device within a patient's body portion.

FIG. 10 illustrates the positioning of an endoscope 10' or 10" and a treatment device 20 within a patient's body portion. In particular, FIG. 10 depicts the extension of a treatment instrument 20 within a particular bile duct 80 during an ERCP procedure. As seen in FIG. 10, the endoscope 10', for example, is inserted and extended through a patient's stomach 82 such that the distal end and aperture 32 (not shown) of endoscope 10' are positioned in close relation to a particular bile duct 80 leading to, for example, gall bladder 84. As seen in FIG. 10, treatment instrument 20 is extended beyond the internal working channel 34 of endoscope 10'. The treatment instrument 20 can then be precisely manipulated, for example, by controlled rotation of tube 36 and deflection of elevator 35, described in FIGS. 4A-7. Alternatively, the instrument 20 can be manipulated using the embodiment of endoscope 10" described in FIGS. 8A-9B. In the embodiment of endoscope 10", manipulation of treatment instrument 20 is effectuated through manipulation of sleeve 60 and pull wire 62.

Precise manipulation of treatment instrument 20 allows for more precise positioning and location of instrument 20 such as, for example, during placement of instrument 20 within a particular bile duct 80 of interest. More precise manipulation of a treatment device 20 can result in shortened treatment procedures by reducing the amount of time necessary to effectuate proper position of the treatment device 20. In addition, controlled deflection of the angle at which treatment device 20 exits the underlying endoscope 10', 10" can reduce internal tissue trauma caused during endoscopic procedures requiring repeated repositioning and manipulation of the entire endoscope. For example, the positioning mechanisms described in FIGS. 4A-9B facilitate the location of treatment instrument 20 within a particular bile duct 80 without repeated manipulation and displacement of the underlying endoscope body. Accordingly, the occurrence of tissue trauma during a treatment procedure can be reduced.

While the above described positioning system has been depicted as utilizing pull wire manipulation mechanisms for effectuating deflection of elevator 35 and sleeve 60, the invention it not intended to be limited to this particular structure. Therefore, alternative actuation devices are intended to be within the scope of this invention, including all equivalent structures known for transferring endoscopic manipulation forces along the longitudinal axis of an endoscope. In addition to the positioning mechanisms disclosed above, the system of this application may further include other additional positioning mechanisms, such as those for achieving controlled deflection of the elongated flexible tube of the endoscope.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An endoscopic device, comprising:
a bendable outer tube comprising a lumen;
a bendable inner tube, comprising:
a distal end, and
a lumen,
wherein the inner tube is received in the lumen of the outer tube, and the inner tube is rotatable relative to the outer tube; and
a positioning mechanism at the distal end of the inner tube, the positioning mechanism comprising a surface for engaging an instrument received in the lumen of the inner tube, wherein the surface is configured to be tilted proximally toward the distal end of the inner tube, and wherein the surface is configured to rotate relative to the outer tube upon rotation of the inner tube relative to the outer tube.

2. The device of claim 1, wherein the positioning mechanism comprises a wire operatively coupled to the surface of the positioning mechanism, and exertion of a force on the wire in a proximal direction tilts the surface toward the distal end of the inner tube.

3. The device of claim 1, wherein the positioning mechanism comprises a lever, and the surface of the positioning mechanism is a surface of the lever.

4. The device of claim 3, wherein the lever is rotatable relative to the distal end of the inner tube, about a hinge coupling the lever and the distal end of the inner tube.

5. The device of claim 1, wherein the outer tube comprises a sidewall with an aperture opening into the lumen of the outer tube.

6. An endoscopic device, comprising:
a bendable outer tube comprising a lumen;
a bendable inner tube, comprising:
a distal end,
a central longitudinal axis extending along a first direction, and
a lumen,
wherein the inner tube is received in the lumen of the outer tube, and the inner tube is rotatable relative to the outer tube about the central longitudinal axis; and
a positioning mechanism at the distal end of the inner tube, the positioning mechanism comprising a surface for engaging an instrument received in the lumen of the inner tube, wherein the surface is configured to be rotated relative to the distal end of the inner tube about a rotational axis extending along a second direction transverse to the first direction, and wherein the surface is configured to rotate relative to the outer tube, about the central longitudinal axis of the inner tube, upon rotation of the inner tube relative to the outer tube.

7. The device of claim 6, wherein the positioning mechanism comprises a lever, and the surface of the positioning mechanism is a surface of the lever.

8. The device of claim 7, wherein the lever is rotatable about the rotational axis and about the central longitudinal axis of the inner tube.

9. The device of claim 7, wherein the lever comprises a proximal end rotatably coupled to a tapering portion of the distal end of the inner tube.

10. The device of claim 7, wherein the lever comprises a distal end coupled to a pull wire, the pull wire extending proximally from the distal end of the lever toward a proximal end of the outer tube.

11. An endoscope system, comprising:
an outer tube comprising a lumen;
a deflection mechanism received in the lumen of the outer tube, the deflection mechanism comprising:
an inner tube, comprising:
a distal end,
a central longitudinal axis, and
a lumen configured to receive an elongate instrument,
wherein the inner tube is rotatable relative to the outer tube, and
a deflection lever rotatably coupled to the distal end of the inner tube, the deflection lever being rotatable relative to the distal end of the inner tube between a first position and a second position, wherein in the first position a portion of the elongate instrument is deflected to a first angle relative to the central longitudinal axis of the inner tube, and in the second position the portion of the elongate instrument is deflected to a second angle relative to the central longitudinal axis of the inner tube, the second angle having a different value than the first angle, and wherein the deflection lever is configured to rotate relative to the outer tube upon rotation of the inner tube relative to the outer tube.

12. The endoscope system of claim 11, wherein the inner tube is rotatable relative to the outer tube about the central longitudinal axis of the inner tube.

13. The endoscope system of claim 11, wherein the deflection mechanism comprises a rotational axis rotatably coupling the deflection lever to the distal end of the inner tube.

14. The endoscope system of claim 13, wherein the rotational axis extends transverse to the central longitudinal axis of the inner tube.

15. The endoscope system of claim 14, wherein the rotational axis comprises a hinge pin.

16. The endoscope system of claim 13, wherein the rotational axis extends through a proximal end of the deflection lever and a tapering portion of the distal end of the inner tube.

17. The endoscope system of claim 11, wherein the deflection mechanism comprises a wire coupled to a distal end of the deflection lever.

18. The endoscope system of claim 17, wherein the wire extends through the outer tube to an endoscope handle, the endoscope handle being configured to selectively exert a proximal force on the wire to pull the distal end of the deflection lever in a proximal direction.

\* \* \* \* \*